(12) United States Patent
Colomb

(10) Patent No.: US 9,616,186 B2
(45) Date of Patent: Apr. 11, 2017

(54) POWDER INHALING DEVICE WITH TWO-PART ROTARY RECEIVING ELEMENT FOR BLISTER STRIP CLOSURE LAYER

(75) Inventor: Arnaud Colomb, Verneuil sur Seine (FR)

(73) Assignee: APTAR FRANCE SAS, Le Neubourg (FR)

( * ) Notice: Subject to any disclaimer, the term of this patent is extended or adjusted under 35 U.S.C. 154(b) by 399 days.

(21) Appl. No.: 14/237,249

(22) PCT Filed: Aug. 13, 2012

(86) PCT No.: PCT/FR2012/051883
§ 371 (c)(1),
(2), (4) Date: May 19, 2014

(87) PCT Pub. No.: WO2013/026976
PCT Pub. Date: Feb. 28, 2013

(65) Prior Publication Data
US 2014/0290653 A1    Oct. 2, 2014

(30) Foreign Application Priority Data
Aug. 19, 2011   (FR) ..................... 11 57410

(51) Int. Cl.
*A61M 15/00*   (2006.01)
(52) U.S. Cl.
CPC .... *A61M 15/0051* (2014.02); *A61M 15/0008* (2014.02); *A61M 15/0026* (2014.02);
(Continued)
(58) Field of Classification Search
CPC .......... A61M 15/0008; A61M 15/0043; A61M 15/0045; A61M 15/0051; A61M 15/0055
See application file for complete search history.

(56) References Cited

U.S. PATENT DOCUMENTS

| 6,427,688 B1 * | 8/2002 | Ligotke ............. A61M 15/0086 128/203.12 |
| 2003/0172927 A1 | 9/2003 | Young et al. |

(Continued)

FOREIGN PATENT DOCUMENTS

| TR | WO 2011049541 A1 * | 4/2011 | ........ A61M 15/0045 |
| WO | 03/035509 A1 | 5/2003 | |

(Continued)

OTHER PUBLICATIONS

English translation of the International Preliminary Report on Patentability for PCT/FR2012/051883.

*Primary Examiner* — Kathryn E Ditmer
(74) *Attorney, Agent, or Firm* — Sughrue Mion, PLLC

(57) ABSTRACT

A powder inhaler having reservoirs containing a dose of powder and formed on a flexible blister strip having a base layer with cavities and a closure layer. The base layer containing empty blisters rolls up around a first rotary receiver element, and the closure layer peeled off the base layer rolls up around a second rotary receiver element that has a first portion forming a peeling wheel and a second portion forming a tensioner. The tensioner is capable of turning in a first direction of rotation and includes a fastener element for the leading end of the closure layer. The tensioner turns with the peeling wheel in the first direction to roll up the closure layer at each actuation of the device and turns relative to the peeling wheel in the first direction of rotation to tension the closure layer after the blister strip has been assembled in the body.

9 Claims, 2 Drawing Sheets

(52) U.S. Cl.
CPC .... *A61M 15/0043* (2014.02); *A61M 15/0045* (2013.01); *A61M 15/0055* (2014.02); *A61M 2202/064* (2013.01)

(56) References Cited

U.S. PATENT DOCUMENTS

| | | | |
|---|---|---|---|
| 2004/0244794 A1* | 12/2004 | Richards | A61K 9/0075 128/203.15 |
| 2005/0228341 A1* | 10/2005 | Edgerley | A61M 15/0045 604/59 |
| 2008/0041368 A1* | 2/2008 | Jones | A61M 15/0045 128/200.23 |
| 2010/0307493 A1* | 12/2010 | Kirniak | A61M 15/0045 128/203.15 |
| 2011/0192397 A1* | 8/2011 | Saskar | A61M 15/0045 128/200.17 |

FOREIGN PATENT DOCUMENTS

| | | |
|---|---|---|
| WO | 2004/067069 A2 | 8/2004 |
| WO | 2006/018261 A1 | 2/2006 |

\* cited by examiner

POWDER INHALING DEVICE WITH TWO-PART ROTARY RECEIVING ELEMENT FOR BLISTER STRIP CLOSURE LAYER

CROSS REFERENCE TO RELATED APPLICATIONS

This application is a National Stage of International Application No. PCT/FR2012/051883, filed on Aug. 13, 2012, which claims priority from French Patent Application No. 1157410, filed on Aug. 19, 2011, the contents of all of which are incorporated herein by reference in their entirety.

The present invention relates to a powder inhaler device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in packaging the doses of powder in individual predosed reservoirs of the blister type, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. However, this makes the devices complex and thus costly to manufacture and to assemble. In devices that use a blister strip, assembling the blister strip may turn out to be complex, in particular when said blister strip is of the peelable type, with a rotary receiver element for receiving the base layer and a rotary receiver element for receiving the closure layer. Thus, in order to guarantee reliable operation, the base and closure layers of the blister strip should always be taut, even though this is precisely what complicates assembly. Documents WO 2006/018261, WO 03/035509, and WO 2004/067069 describe prior-art devices.

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble that is reliable in use, with good metering accuracy that is reproduced on each actuation.

The present invention thus provides a powder inhaler device comprising a body provided with a dispenser orifice, a plurality of predosed reservoirs, each containing a dose of powder to be dispensed, said plurality of reservoirs being formed on an elongate flexible blister strip comprising a base layer that contains the cavities of the reservoirs, and a closure layer overlying said cavities, the closure layer being peelable off the base layer, the portion of base layer containing the empty blisters rolling up around a first rotary receiver element, and the portion of closure layer peeled off said base layer rolling up around a second rotary receiver element, the device being characterized in that said second rotary receiver element is constituted by two portions, a first portion forming a peeling wheel, and a second portion forming a tensioner, said tensioner being snap-fastened on said peeling wheel and being capable of turning relative to said peeling wheel in a first direction of rotation only, said tensioner including a fastener element that receives the leading end of said closure layer, said tensioner turning together with said peeling wheel in said first direction of rotation so as to roll up said closure layer at each actuation of the device, and said tensioner being capable of turning relative to said peeling wheel in the first direction of rotation so as to tension said closure layer after the blister strip has been assembled in the body.

Advantageously, said peeling wheel includes an inner set of teeth co-operating with pawl-forming flexible fingers of the tensioner, which pawls enable the tensioner to turn relative to said peeling wheel in said first direction of rotation, but prevent it from turning in the opposite direction.

Advantageously, the device includes displacement means, such as an indexer wheel, so as to cause the blister strip to advance before and/or during each actuation, said second rotary receiver element being correlated in rotation with said indexer wheel.

Advantageously, said peeling wheel includes an outer set of teeth meshing in rotary manner with said indexer wheel.

Advantageously, said tensioner includes flexible blades that are adapted to compress radially as the closure layer rolls up.

Advantageously, the leading end of the base layer is fastened to said first rotary receiver element that is provided with a spiral spring so as to exert tension on said base layer.

Advantageously, the device includes a dispersion chamber including both an inlet that, during inhalation, is connected to an open reservoir, and receives the flow of air and of powder from said open reservoir via a delivery channel, and also an outlet that is connected to said dispenser orifice via a dispenser channel, said dispersion chamber including at least one ball that is movable in said dispersion chamber, said dispersion chamber including at least one approximately tangential air inlet, said delivery and dispenser channels extending in a same direction that is substantially perpendicular to said at least one tangential air inlet of said dispersion chamber.

Advantageously, said device includes means for unsticking said closure layer from said base layer, such as a peeling edge around which said closure layer extends.

Advantageously, said dispersion chamber contains a plurality of balls.

These characteristics and advantages and others of the present invention appear more clearly from the following detailed description, given by way of non-limiting example, and with reference to the accompanying drawing, and in which.

Figure 1:
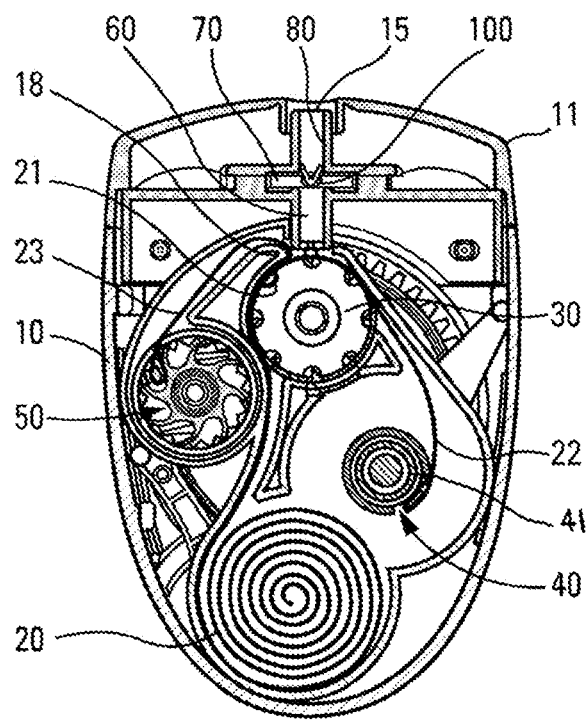
FIG. 1 is a diagrammatic section view of a powder inhaler device in an advantageous embodiment of the invention, after assembling the blister strip and before putting the base and closure layers of said blister strip under tension.
Figure 2:
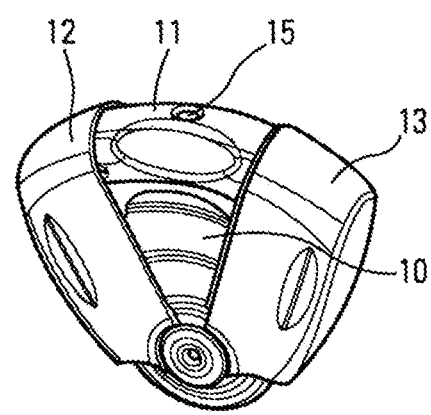
FIG. 2 is a diagrammatic perspective view of the device with the cover portions open.

FIG. 1 shows an advantageous variant embodiment of a dry-powder inhaler. The inhaler includes a body 10 on which there can be slidably or pivotally mounted two cover-forming portions 12, 13 that are visible in FIG. 2 and that are adapted to be opened so as to open and prime the device. In a variant, a single cover portion is also possible. The body 10 can be approximately rounded in shape, but it could be of any other appropriate shape. The body 10 includes a mouthpiece 11 that defines a dispenser orifice 15 through which the user inhales while the device is being actuated.

Inside the body 10 there is provided a strip 20 of individual predosed reservoirs 21, also known as blisters, said strip being made in the form of an elongate flexible strip on which the blisters are arranged one behind another, in manner known per se. The blister strip 20 is of the peelable type with a base layer 22 including the cavities forming the blisters, and a peelable closure layer 23 that progressively unsticks from the base layer 22 on each actuation.

Before first use, the blister strip 20 can be rolled up inside the body 10, preferably in a storage portion, and displacement means 30 for displacing the strip are provided for progressively unrolling the blister strip 20 and for causing it to advance. The base-layer portion 22 including the empty cavities is advantageously adapted to be rolled up in another location of said body 10, in particular a first receiver portion, and the unstuck closure-layer portion 23 is advantageously adapted to be rolled up in yet another location of said body 10, in particular a second receiver portion.

The first reception portion advantageously comprises a first rotary receiver element 40, around which the base-layer portion 22 including the empty cavities is rolled up. Advantageously, the first rotary receiver element 40 is urged to turn by a spring 41, in particular a spiral spring that is arranged inside said first rotary element. This guarantees proper rolling up on each actuation.

The second receiver portion advantageously comprises a second rotary receiver element 50, around which the unstuck closure-layer portion 23 rolls up. The second rotary receiver element 50 is also urged to turn, in particular being correlated in rotation with the displacement means 30 of the blister strip 20. This guarantees proper rolling up on each actuation.

The displacement means 30 are adapted to cause the blister strip 20 to advance before and/or during each actuation of the device. The displacement means preferably comprise an indexer wheel 30 that receives and guides the blisters. Turning the indexer wheel 30 causes the blister strip 20 to advance. Advantageously, the indexer wheel 30 is turned when the device is primed, e.g. by opening the cap.

In an advantageous aspect, the inhaler includes a dispersion chamber 70 for receiving the dose of powder after a respective reservoir has been opened. The dispersion chamber 70 includes an inlet that is connected directly to the open reservoir via a powder delivery channel 60, and an outlet that is connected directly to the dispenser orifice 15 via a powder dispenser channel 80. The dispersion chamber 70 preferably contains at least one ball 71, advantageously a plurality of balls, e.g. three balls. The balls 71 may move in said dispersion chamber 70 along a ball path that is substantially circular and that extends in a plane that is approximately transverse to the orientation of the delivery and dispenser channels 60 and 80. The dispersion chamber 70 includes at least one, preferably two tangential air inlets. In this way, the flows of air entering via the tangential air inlets swirl in the dispersion chamber 70 and cause the balls 71 to turn. The flows of air that are created by the user inhaling are mixed with the flow of air and of powder that comes from the open reservoir through the delivery channel 60, and that penetrates into the dispersion chamber 70. The flow of air and of powder is thus also caused to turn in the dispersion chamber 70, and the balls 71 break up the powder before said powder is driven from the dispersion chamber 70 towards the dispenser orifice 15 via said dispenser channel 80. Optionally, a deflector 100 may be provided at the location where the powder delivery channel 60 opens out into the dispersion chamber 70, in particular when said delivery channel 60 is coaxial to, and in alignment with, the dispenser channel 80, as shown in FIG. 1. The makes it possible to deflect the flow of air and of powder coming from the open reservoir, and to avoid said flow of air and of powder flowing directly into the dispenser channel 80. Naturally, other shapes and positions of the delivery and dispenser channels are possible.

When the device is actuated, the indexer wheel 30 is turned, and this brings the next blister 21 to face the delivery channel 60. Simultaneously, the closure-layer 23 is removed from the blister 21, being peeled off by turning the second rotary receiver element 50 that is correlated in rotation with the indexer wheel 30. Advantageously, the closure layer extends around a stationary peeling corner 18 that, in association with the simultaneous turning of the indexer wheel 30 and of the second rotary receiver element 50, causes the closure layer 23 to be unstuck from or peeled off the base layer 22 at said peeling corner 18. The base layer 22 downstream from the indexer wheel 30 rolls up around the first rotary receiver element 40. Thus, an open blister 21 is situated facing the delivery channel 60. When the user inhales, a first flow of air is created through an air delivery channel, which flow of air passes through the open blister and thus drives the powder in the form of a flow of air and of powder into the delivery channel 60. Simultaneously, the inhalation creates secondary flows of air that penetrate tangentially into the dispersion chamber 70 through the tangential air inlets. The secondary flows of air cause the balls 71 to turn in the dispersion chamber 70. When the flow of air and of powder encounters the secondary flows of air and the balls moving in the dispersion chamber 70, swirls are created, and this fluidifies and breaks up the powder that finally escapes towards the dispenser orifice 15.

Naturally, the dimensions and orientations of the various channels may be optimized depending on the features of the inhaler, so as to maximize the performance thereof.

In order to guarantee reliable operation of the device, the base layer 22 and the closure layer 23 that roll up around the first and second rotary receiver elements 40, 50 respectively, need to be taut. However, while the blister strip is being assembled in the body 10, it is desirable to avoid tensioning those portions of the blister strip. Thus, as can be seen in FIG. 1, which shows the blister strip after it has been assembled, both the closure layer 23 and the base layer are relaxed, thereby making assembly easier.

At the base layer 22 and the first receiver element 40, said receiver element may include a spiral spring that provides traction on said base layer after it has been assembled.

With regard to the closure layer 23, it is fastened to a second receiver element 50 that is formed of two portions. A first portion 51 that is referred to as a peeling wheel, and a second portion 52 that is referred to as a tensioner and that is assembled on said first portion. In the description below, the two portions are designated by the terms peeling wheel 51 and tensioner 52.

The peeling wheel 51 comprises a central sleeve that, on one end, includes a disk that is provided with an outer set of teeth 57 that mesh with a corresponding set of teeth (not shown) of the indexer wheel 30. Thus, each turn of the indexer wheel causes the peeling wheel 51 to turn in a first direction. The disk of the peeling wheel also includes an inner set of teeth 56, for a purpose that is described below. On the other end of the sleeve, the peeling wheel includes a snap-fastener profile 58.

Figure 7:
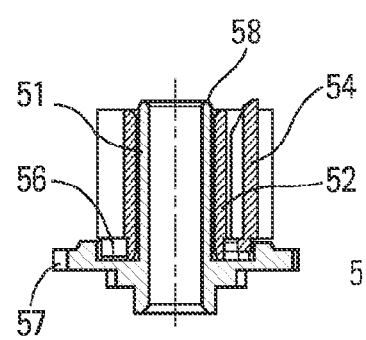
FIGS. 7 and 8 are cross-section views on various sections showing the receiver element for receiving the closure layer of the blister strip, in its assembled position.
Figure 8:
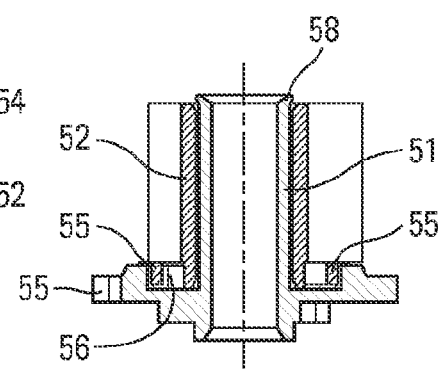
Figure 9:
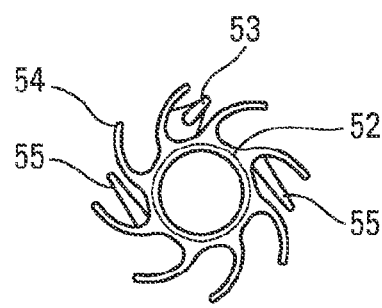
FIG. 9 is a diagrammatic plan view of a detail of a portion of said receiver element for receiving the closure layer.
Figure 10:
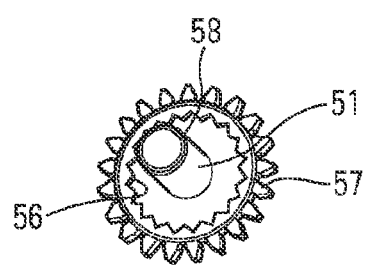
FIG. 10 is a diagrammatic plan view of a detail of the other portion of said receiver element for receiving the closure layer.

The tensioner 52 includes a hollow central sleeve that is assembled around the central sleeve of the peeling wheel, and that has a top edge that comes to snap-fastening below the snap-fastener profile 58 of the peeling wheel, as can be seen in FIGS. 7 and 8. On its opposite end, the tensioner includes two flexible fingers 55 that are preferably diametrally opposite and that co-operate with the inner set of teeth 56 of the peeling wheel so as to form pawls. The tensioner 52 may thus turn about the peeling wheel 51, but only in said first direction of rotation. The tensioner also includes a fastener element 53 for fastening the front end of the closure layer 23 of the blister strip, and flexible blades 54 that are capable of deforming radially inwards as said closure layer 23 rolls up. The progressive deformation of the flexible blades 54 makes it possible to keep the closure layer under tension even when the outside diameter of the roll increases while the peeling wheel 51 turns through steps of constant size.

Figure 3:
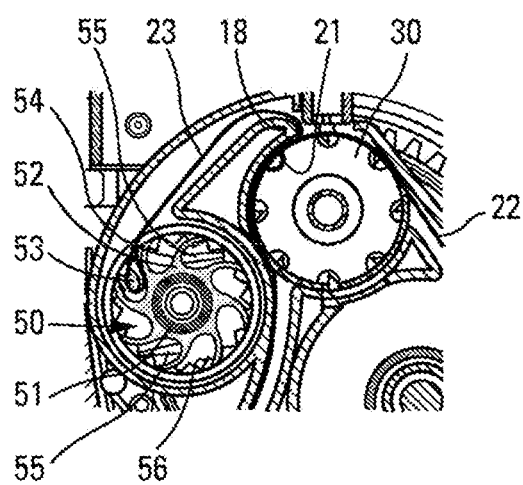
FIGS. 3 and 4 are cross-section views of a detail of a portion of the FIG. 1 device, respectively before and after putting the closure layer under tension.
Figure 4:
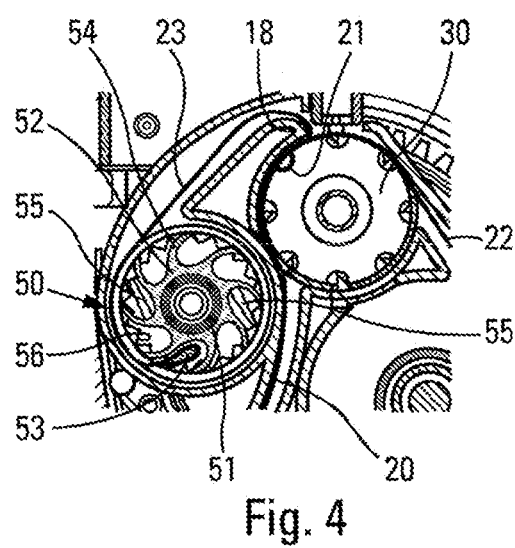
Figure 5:
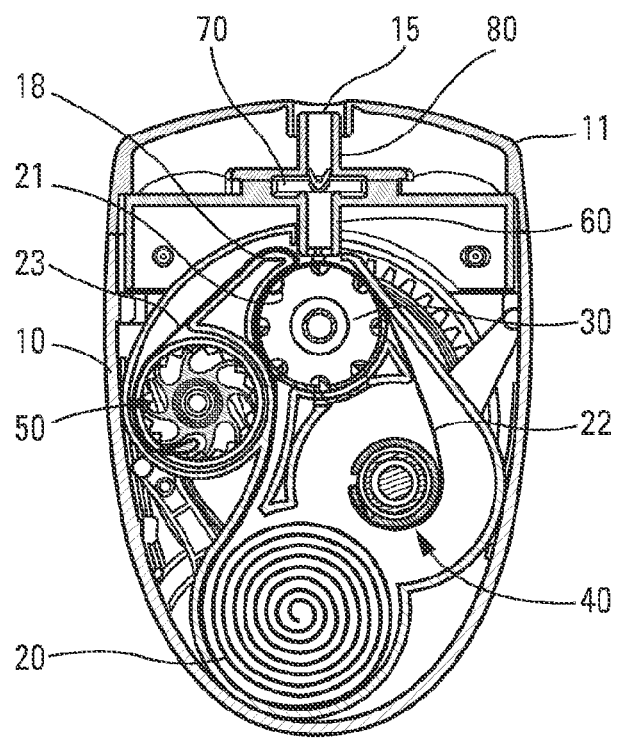
FIG. 5 shows a view similar to the view in FIG. 1, after assembling the blister strip and after putting the base and closure layers of said blister strip under tension.
Figure 6:
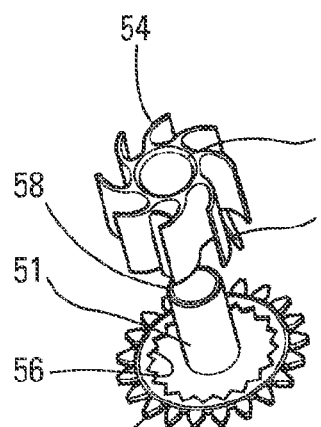
FIG. 6 is an exploded diagrammatic perspective view of the receiver element for receiving the closure layer of the blister strip.

During assembly, the closure layer is not taut so as to make assembly easier. The peeling wheel 51 may thus be prevented from turning, by directly blocking said peeling wheel 51 or by blocking the indexer wheel 30, and the tensioner 52 may then be turned relative to the peeling wheel 51 in said first direction of rotation so as to tension said closure layer 23. The tensioning operation is shown in FIGS. 3 and 4. Subsequently, each turn of the peeling wheel 51 in the first direction of rotation causes a corresponding turn of the tensioner 52, and thus a progressive rolling up of the closure layer 23 around said second rotary receiver element 50.

Various modifications are possible for the skilled person without departing from the scope of the present invention as defined in the accompanying claims.

The invention claimed is:

1. A powder inhaler device comprising a body provided with a dispenser orifice, a plurality of predosed reservoirs, each containing a dose of powder to be dispensed, said plurality of reservoirs being formed on an elongate flexible blister strip comprising a base layer that contains the cavities of the reservoirs, and a closure layer overlying said cavities, the closure layer being peelable off the base layer, the portion of base layer containing the empty blisters adapted to be rolled up around a first rotary receiver element, and the portion of closure layer peeled off said base layer adapted to be rolled up around a second rotary receiver element, wherein said second rotary receiver element is constituted by two portions, a first portion forming a peeling wheel, and a second portion forming a tensioner, said tensioner comprising a hollow first central sleeve, pawl-forming flexible fingers, a fastener element and flexible blades, said hollow first central sleeve being snap-fastened onto a second central sleeve of said peeling wheel such that said tensioner is capable of turning relative to said peeling wheel in a first direction of rotation only, said fastener element adapted to receive a leading end of said closure layer, wherein said peeling wheel includes an inner set of teeth co-operating with said pawl-forming flexible fingers of the tensioner, which enable the tensioner to turn relative to said peeling wheel in said first direction of rotation, but prevent the tensioner from turning in the opposite direction, wherein the flexible blades are adapted to compress radially as the closure layer rolls up, said tensioner adapted to turn together with said peeling wheel in said first direction of rotation so as to roll up said closure layer at each actuation of the device, and said tensioner being capable of turning relative to said peeling wheel in the first direction of rotation so as to tension said closure layer after the blister strip has been assembled in the body.

2. A device according to claim 1, wherein the device includes displacement means, to cause the blister strip to advance before and/or during each actuation, said second rotary receiver element being correlated in rotation with said displacement means.

3. The device according to claim 2, wherein the device displacement means is an indexer wheel.

4. A device according to claim 2, wherein said peeling wheel includes an outer set of teeth meshing in rotary manner with said indexer wheel.

5. A device according to claim 1, wherein a leading end of the base layer is fastened to said first rotary receiver element that is provided with a spiral spring so as to exert tension on said base layer.

6. A device according to claim 1, wherein the device includes a dispersion chamber including both an inlet that, during inhalation, is connected to an open reservoir, and receives a flow of air and of powder from said open reservoir via a delivery channel, and also an outlet that is connected to said dispenser orifice via a dispenser channel, said dispersion chamber including at least one ball that is movable in said dispersion chamber, said dispersion chamber including at least one approximately tangential air inlet, said delivery and dispenser channel extending in a same direction that is substantially perpendicular to said at least one tangential air inlet of said dispersion chamber.

7. A device according to claim 6, wherein said dispersion chamber contains a plurality of balls.

8. A device according to claim 1, wherein said device includes means for unsticking said closure layer from said base layer.

9. The device according to claim 8, wherein the means for unsticking said closure layer from said base layer is a peeling edge around which said closure layer extends.

* * * * *